United States Patent [19]

Marconi et al.

[11] 4,248,704
[45] Feb. 3, 1981

[54] PHENYLALANINE AMMONIA LYASE OCCLUDED FIBERS FOR REDUCING PHENYLALANINE BLOOD-LEVEL

[75] Inventors: Walter Marconi, Milan; Francesco Bartoli, Rome; Roberto Gianna, Rome; Franco Morisi, Rome; Giuseppina Spotorno, Rome, all of Italy

[73] Assignee: Snamprogetti S.p.A., Milan, Italy

[21] Appl. No.: 35,528

[22] Filed: May 3, 1979

[30] Foreign Application Priority Data

May 12, 1978 [IT] Italy ............................... 23336 A/78

[51] Int. Cl.³ ............................................. B01D 13/00
[52] U.S. Cl. ..................................... 210/632; 210/36; 435/232; 435/269
[58] Field of Search ............... 435/182, 288, 269, 267, 435/177, 227, 232; 210/2, 23 F, 22, 433 M, 500 M, DIG. 23, 321 B, 36, 502, 506; 536/56, 61, 76, 85; 548/233

[56] References Cited

U.S. PATENT DOCUMENTS

| | | | |
|---|---|---|---|
| 3,228,877 | 1/1966 | Mahon | 210/22 |
| 3,441,142 | 4/1969 | Oja | 210/321 B |
| 3,522,346 | 7/1970 | Chang | 210/22 |
| 3,673,612 | 7/1972 | Merrill et al. | 210/22 |
| 3,809,613 | 5/1974 | Vieth et al. | 435/288 |
| 3,875,008 | 4/1975 | Yoshino et al. | 435/182 |
| 4,004,980 | 1/1977 | Emery et al. | 435/182 |
| 4,051,040 | 9/1977 | Hazdra et al. | 210/321 B |
| 4,127,481 | 11/1978 | Malchesky et al. | 210/22 A |

FOREIGN PATENT DOCUMENTS

836462  2/1969  Italy ........................................ 435/182

OTHER PUBLICATIONS

"Phenylalanine ammonia-Lyase" Fritz et al, Journ. of Biol. Chem. vol. 251, No. 15, Aug. 1976 pp. 4646-4650.
"Fibre-Entrapped Enzymes" Dinecci, Process Biochemistry, Aug. 1972, pp. 9-12.

*Primary Examiner*—Charles N. Hart
*Assistant Examiner*—David R. Sadowski
*Attorney, Agent, or Firm*—Morgan, Finnegan, Pine, Foley & Lee

[57] ABSTRACT

Phenylalanine level in blood or another medium is considerably reduced and can even be annulled by causing blood or the other medium to flow through a mass of porous fibers in which the enzyme phenylalanine ammonia lyase has been occluded: the fibers have been previously made biocompatible, if necessary.

1 Claim, No Drawings

PHENYLALANINE AMMONIA LYASE OCCLUDED FIBERS FOR REDUCING PHENYLALANINE BLOOD-LEVEL

This invention relates to a composition which is capable of reducing the phenylalanine blood-level, or of reducing the phenylalanine concentration in phenylalanine-containing media, and relates also to the method for using such a composition.

It is known that phenylalanine is an essential aminoacid. However, in addition to playing a role in the synthesis of proteins, this aminoacid, together with tyrosine, is the base substance for synthesizing cathecolamines, adrenaline, thyroidal hormones (triiodo- and tetraiodotyrosine) and the physiological pigment melanine.

The starting step for the formation of these substances is the oxidation of phenylalanine and tyrosine, which takes place in the liver by the action of phenylalanine hydroxylase.

Blocking this enzymic reaction is conducive to an accumulation of phenylalanine in blood.

As a result, an alternative katabolic route is originated, which, upon a transamination of phenylalanine to phenylpyruvic acid, is conductive to phenylacetic acid which is eliminated through the urinary tract.

From a medical standpoint, such a metabolic block is known as the phenylketonuria, or phenylpyruvic disease or also Fölling's disease. It is a congenital disease and is hereditary, as transmitted with a simple recessive character, which affects both sexes indiscriminately, especially in North-European countries. It causes mental retardation, convulsions, eczema, defective skin pigment formation.

An excess of phenylalanine, on the other hand, alters the metabolism of both trytophan and tyrosine.

Oxidation of tryptophan is inhibited, with attendant splitting of the indole ring and formation of formylkynurein, hydroxylation to 5-hydroxytryptophan and the decarboxylation of the latter to 5-hydroxytryptamine.

Tryptophan must thus have an ancilliary metabolic route available which involves the excretion through the urinary tract of indolpyruvic, indol lactic and indol acetic acids in amounts which are even 20 times higher than those of the normal subjects.

An excess of phenylalanine inhibits tyrosinase and thus the formation of melanin is hindered.

Phenylpyruvic acid, in its turn, inhibits, at least partially, the oxidation of tyrosine to gentisinic acid and the formation of cathecolamines due to the inhibition of the dopa-decarboxylase.

The mental pathogenesis is presumably attributable, rather than to a direct toxic action of phenylalanine on the cerebral metabolism, to the reduced production of the neurohumoral agents which are essential for a normal evolution of the cerebral functions, such as serotonin, cathecolamines.

The present therapeutical approach is alimentary only.

A phenylalanine-poor diet is adopted, in which phenylalanine must generally be kept below 10-30 milligrams per kilogram by daily. Proteinic hydrolysates with a low phenylalanine percentage are used to this purpose.

Lastly, a few authors surmise that the elimination of phenylalanine may reduce the development of leukaemic cells. It would be theoretically possible to reduce the phenylalanine blood level. As a matter of fact, there is an enzyme, the phenylalanine ammonia lyase, which converts phenylalanine into cinnamic acid and ammonia. It is impossible, regrettably, to introduce such an enzyme directly in the blood stream, due to the marked antigenic character of the enzyme which causes, after one or two administrations, a quick elimination of the enzyme itself.

In this connection see, for example, the article by R. R. Fritz, D. S. Hodgins and C. W. Abell in the J. of Biol. Chem. vol. 251, page 4646 of 1976. These authors have administered the enzyme to test animals and have seen that the halving times obtained with the first administration (22 hours) are considerably shortened in the subsequent administrations. The presence of an antibody which is specific for the enzyme is concurrently observed.

It has now been found, that which is the object of the present invention, that it is possible to exploit this enzyme in the blood stream of patients affected by phenylketonuria without experiencing the enzyme-rejection phenomenon due to a long stay of the enzyme in the blood stream.

The enzyme has been immobilized, according to the method described in the Italian Patent No. 836 462 of the same Assignee hereof, in porous fibres of cellulose triacetate which have been rendered biocompatible by adding to the polymeric phase a platelet aggregation preventing agent such as 4,5-diphenyl-2-bis(2-hydroxyethyl) amino oxazole. By so doing, a composition is provided which permits to adjust the concentration of the phenylalanine which is present in the blood without having the proteinic catalyst which is used in direct contact with the blood.

In addition, the high surface to volume ratio minimizes the diffusion effects, that is, the rapidity of access of the substrate to the catalytic sites.

The material so prepared possesses biocompatibility that is, it can be used without any intervening troubles such as platelet adhesion, formation of thrombi and others.

Lastly, the material can be used in the treatment of proteinic hydrolysates to be used as food in order selectively to reduce the phenylalanine contents within a range which can be tolerated by phenylketonuria patients.

Heretofore, the route for producing food adapted to the assumption by phenylketonuria patients involved cumbersome chromatographic separation stages of proteinic hydrolysates and subsequent reconstitution of a properly proportional mixture from which phenylalanine is excluded. The present invention, conversely, makes it possible to remove phenylalanine from proteinic hydrolysates by merely treating these with the fibres aforementioned.

For details on the preparation and use of such materials, reference is invited to the scrutiny of the working examples by means of which we intend that the invention be illustrated without limiting its scope, as it will be easy for a technician, once the principle of the invention has been appraised, to vary the nature of the ingredients and the mode of use so as to purify the blood in the sense intended herein.

EXAMPLE 1

To a solution composed by 20 g of cellulose triacetate and 7 g of 4,5-diphenyl-2-bis(2-hydroxyethyl) amino oxazole in 930 mls of methylene chloride, there have been added at 2° C., 140 mls of a solution of the phenylalanine ammonia lyase in a Tris buffer (0.05 M HCl, pH 7.5) also containing 30% glycerol. The enzyme solution has been obtained by extracting the enzyme from *Rhodotorula glutinis* and purifying it by precipitations with protamine sulfate, ammonium sulfate and sodium citrate to a specific activity of 2.1 micromols/min.milligram of protein.

The activity of the solution was 113 U per milliliter.

By stirring, an emulsion has been obtained, which has then been extruded, under nitrogen pressure, through a spinneret immersed in a coagulation bath formed by toluene. In the toluene bath there has been formed, by coagulation of the polymer, a fiber which has been taken up on drums and treated with a nitrogen stream to dispel the spinning solvents.

Two grams of fiber have been arranged in the form of an annulus on the walls of a nylon tube having an inside diameter of 7 mm and a length of 500 mm. The walls of the nylon tube had previously been treated according to the method disclosed in the U.S. patent application Ser. No. 917,568 filed on June 21, 1978, in order to make the tube walls non-thrombogenic.

A second enzymic reactor has been prepared with the same procedure as above.

The two reactors have been serially connected and inserted in a system composed by a reservoir, thermostatically controlled at 37° C., and a peristaltic pump and, of course, both reactors.

The reservoir has been charged with 400 mls of blood, supplemented by sodium citrate and phenylalanine (0.7 micromols per milliliter).

Blood has been caused to flow through the reactor at a rate of flow of 4 mls a second. Phenylalanine blood-level assays were periodically effected. The values which have been obtained are reported in the tabulation below:

| Time, mins. | Phenylalanine, micromols per milliliter |
|---|---|
| 0 | 0.70 |
| 15 | 0.55 |
| 30 | 0.42 |
| 60 | 0.23 |

| Time, mins. | Phenylalanine, micromols per milliliter |
|---|---|
| 90 | 0.07 |

This tabulation indicates that under the conditions which have been adopted, phenylalanine is removed from blood in about 90 minutes. The test has been repeated six times again with the same reactors and the total removal of phenylalanine has been achieved in 90 minutes in each case.

EXAMPLE 2

Two enzymic reactors arranged as described in Example 1 and placed in serial arrangement have been used for an extracorporeal circulation by taking blood from the femoral artery and sending it into the femoral vein after having been caused to flow through the enzymic reactors.

Prior to inserting the reactors, 0.1 micromol per milliliter had been found in the blood. After 120 minutes, the phenylalanine blood-level was virtually zero.

EXAMPLE 3

A fiber has been prepared according to the procedure disclosed in Example 1 hereof but by excluding, in this test, the addition of platelet aggregation preventing agents.

5 grams of fiber have been inserted in a thermostatically controlled tubular reactor having a diameter of 40 mm and a height of 220 mm. The reactor has been fed by a casein hydrolysate in 0.4% concentration in phosphate buffer (0.01 M, pH 7.5) at a rate of flow of 600 milliliters an hour: the concentration of phenylalanine was 0.62 micromols per milliliter and that of tyrosine was 0.45 micromols per milliliter.

In the effluent from the column, the concentration of phenylalanine was 0.04 micromols per milliliter, whereas the concentration of tyrosine was 0.05 micromols per milliliter.

We claim:

1. Method for the reduction of the phenylalanine level in blood or another medium containing phenylalanine, consisting in contacting said blood or said media with a composition which comprises the enzyme phenylalanine ammonia lyase occluded in porous fibers of cellulose triacetate which have been made biocompatible by dispersing therein 4,5-diphenyl-2-bis(2-hydroxyethyl) amino oxazole.

* * * * *